(12) United States Patent
Canu et al.

(10) Patent No.: US 8,234,124 B2
(45) Date of Patent: Jul. 31, 2012

(54) ALLERGY PREVENTION

(75) Inventors: Marco Canu, Rome (IT); Sandro Piccinini, Rome (IT); Luigi Pichetti, Rome (IT); Marco Secchi, Rome (IT)

(73) Assignee: International Business Machines Corporation, Armonk, NY (US)

(*) Notice: Subject to any disclaimer, the term of this patent is extended or adjusted under 35 U.S.C. 154(b) by 820 days.

(21) Appl. No.: 12/103,787

(22) Filed: Apr. 16, 2008

(65) Prior Publication Data
US 2009/0265381 A1  Oct. 22, 2009

(51) Int. Cl.
*G06Q 50/00* (2006.01)
(52) U.S. Cl. .............................. 705/2; 705/3
(58) Field of Classification Search .......... 705/2, 3
See application file for complete search history.

(56) References Cited

U.S. PATENT DOCUMENTS

| | | | |
|---|---|---|---|
| 6,652,455 B1* | 11/2003 | Kocher | 600/300 |
| 2002/0095387 A1* | 7/2002 | Sosa et al. | 705/65 |
| 2003/0088439 A1* | 5/2003 | Grushka | 705/2 |
| 2003/0204417 A1* | 10/2003 | Mize | 705/2 |
| 2004/0103033 A1* | 5/2004 | Reade et al. | 705/16 |
| 2004/0249666 A1* | 12/2004 | Napolitano et al. | 705/2 |
| 2008/0183588 A1* | 7/2008 | Agrawal et al. | 705/16 |

* cited by examiner

*Primary Examiner* — Gerald J. O'Connor
*Assistant Examiner* — Neha Patel
(74) *Attorney, Agent, or Firm* — Yee & Associates, P.C.; Jeffrey S. LaBaw

(57) ABSTRACT

An allergy prevention method and system. The method includes retrieving, by a computing system from a fidelity card, a user profile comprising information specifying first elements known to cause a user to have an allergic reaction. The computing system retrieves data associated with an item for purchase. The data comprises information specifying second elements comprised by the item. The computing system compares the first elements to the second elements to determine that a first element of the first elements matches a second element of the second elements. The computing system generates and presents to the user, a warning indicating that the first item may cause the user to have an allergic reaction.

13 Claims, 4 Drawing Sheets

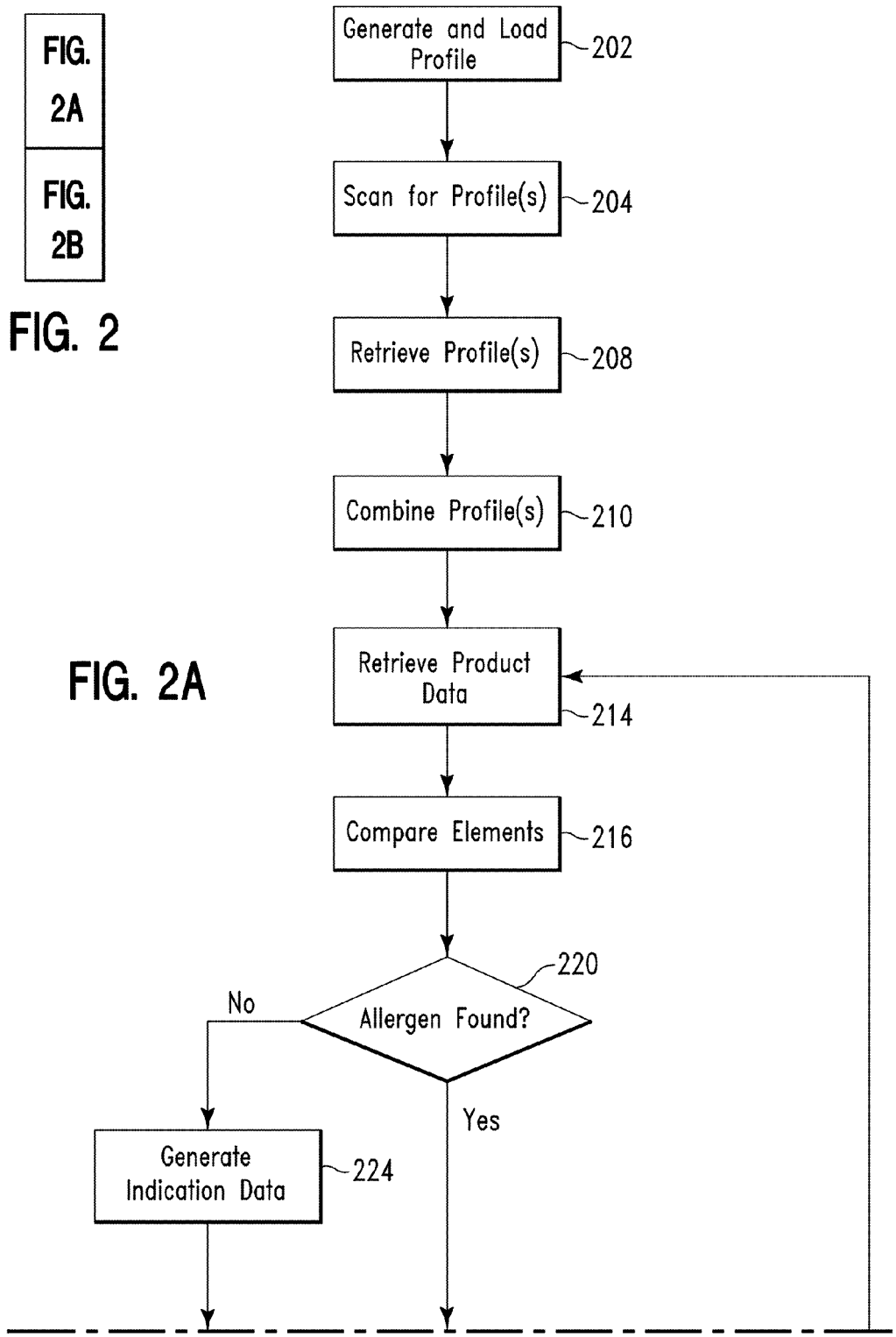

1

ALLERGY PREVENTION

FIELD OF THE INVENTION

The present invention relates to a method and associated system for preventing a user from purchasing items that may cause an allergic reaction.

BACKGROUND OF THE INVENTION

Preventing individuals from obtaining products that may cause harm typically comprises an inefficient process with little flexibility. Accordingly, there exists a need in the art to overcome at least some of the deficiencies and limitations described herein above.

SUMMARY OF THE INVENTION

The present invention provides an allergy prevention method comprising:

scanning, by a computing system, a fidelity card belonging to a first user;

receiving, by said computing system from said first user, a first command for retrieving a first user profile from said fidelity card, wherein said first user profile comprises information specifying a first plurality of elements known to cause said first user to have an allergic reaction;

retrieving, by said computing system from said fidelity card, said first user profile;

retrieving, by said computing system, first data embedded within a first package associated with a first item for purchase, wherein said first data comprises information specifying a second plurality of elements comprised by said first item;

comparing, by said computing system, said first plurality of elements to said second plurality of elements;

first determining, by said computing system based on said comparing said first plurality of elements to said second plurality of elements; that a first element of said first plurality of elements matches a second element of said second plurality of elements;

generating, by said computing system, a warning indicating to said first user that said first item may cause said first user to have an allergic reaction;

presenting, by said computing system, said warning to said first user;

disabling, by said computing system, said first user from purchasing said first item;

retrieving, by said computing system, second data embedded within a second package associated with a second item for purchase, wherein said second data comprises information specifying a third plurality of elements comprised by said second item;

comparing, by said computing system, said first plurality of elements to said third plurality of elements;

second determining, by said computing system based on said comparing said first plurality of elements to said third plurality of elements, that no elements of said first plurality of elements match any elements of said third plurality of elements;

generating, by said computing system, indication data indicating to said first user that said second item is safe for said first user;

presenting, by said computing system, said indication data to said first user;

enabling, by said computing system, said first user to purchase said second item;

generating, by said computing system, a first report indicating results of said first determining and said second determining;

presenting, by said computing system said first report to said first user; and removing said first user profile from said computing system.

The present invention provides an allergy prevention method comprising:

scanning, by a computing system in a shopping cart, a SIM card belonging to a first user, wherein said computing system comprises a SIM card reader and an RFID device reader;

receiving, by said computing system from said first user, a first command for retrieving a first user profile from said SIM card, wherein said first user profile comprises information specifying a first plurality of elements known to cause said first user to have an allergic reaction;

retrieving, by said computing system from said SIM card, said first user profile;

retrieving, by said computing system, first data embedded within a first RFID tag attached to a first package associated with a first item for purchase, wherein said first data comprises information specifying a second plurality of elements comprised by said first item;

comparing, by said computing system, said first plurality of elements to said second plurality of elements;

first determining, by said computing system based on said comparing said first plurality of elements to said second plurality of elements; that a first element of said first plurality of elements matches a second element of said second plurality of elements;

generating, by said computing system, a warning indicating to said first user that said first item may cause said first user to have an allergic reaction;

presenting, by said computing system, said warning to said first user;

disabling, by said computing system, said first user from placing said first item in said shopping cart;

retrieving, by said computing system, second data embedded within a second RFID tag attached to a second package associated with a second item for purchase, wherein said second data comprises information specifying a third plurality of elements comprised by said second item;

comparing, by said computing system, said first plurality of elements to said third plurality of elements;

second determining, by said computing system based on said comparing said first plurality of elements to said third plurality of elements, that no elements of said first plurality of elements match any elements of said third plurality of elements;

generating, by said computing system, indication data indicating to said first user that said second item is safe for said first user;

presenting, by said computing system, said indication data to said first user;

enabling, by said computing system, said first user to place said second item into said shopping cart;

generating, by said computing system, a first report indicating results of said first determining and said second determining;

presenting, by said computing system said first report to said first user; and removing said first user profile from said computing system.

The present invention provides an allergy prevention method comprising:

scanning, by a computing system in a shopping cart, a SIM card belonging to a first user, wherein said computing system comprises a SIM card reader, a credit card reader, and an RFID device reader;

receiving, by said computing system from said first user, a first command for retrieving a first user profile from said SIM card, wherein first user profile comprises first information specifying a first plurality of elements known to cause said first user to have an allergic reaction;

retrieving, by said computing system from said SIM card, said first user profile;

scanning, by said computing system, a credit card belonging to said first user;

receiving, by said computing system from said first user, a second command for retrieving a second user profile from said credit card, wherein said second user profile comprises second information specifying a second plurality of elements known to cause said first user to have an allergic reaction;

retrieving, by said computing system from said credit card, said second user profile;

generating, by said computing system, a third user profile from said first user profile and said second user profile;

retrieving, by said computing system, first data embedded within a first RFID tag attached to a first package associated with a first item for purchase, wherein said first data comprises information specifying a third plurality of elements comprised by said first item;

comparing, by said computing system, said first plurality of elements and second plurality of elements to said third plurality of elements;

first determining, by said computing system based on said comparing said first plurality of elements and second plurality of elements to said third plurality of elements; that a first element of said first plurality of elements matches a second element of said third plurality of elements;

generating, by said computing system, an audible warning indicating to said first user that said first item may cause said first user to have an allergic reaction;

transmitting, by said computing system, said audible warning to a cellular telephone belonging to said first user;

enabling, by said computing system, a first solenoid attached to a door on said shopping cart resulting in shutting said door and preventing said user from placing said first item in said shopping cart;

sensing, by said computing system, that said first item in not within a specified proximity said shopping cart;

disabling, by said computing system, said first solenoid resulting in opening said door and allowing said user to place items in said shopping cart;

retrieving, by said computing system, second data embedded within a second RFID tag attached to a second package associated with a second item for purchase, wherein said second data comprises information specifying a fourth plurality of elements comprised by said second item;

comparing, by said computing system, said first plurality of elements and second plurality of elements to said fourth plurality of elements;

second determining, by said computing system based on said comparing said first plurality of elements and second plurality of elements to said fourth plurality of elements, that no elements of said first plurality of elements and second plurality of elements match any elements of said fourth plurality of elements;

generating, by said computing system, indication data indicating to said first user that said second item is safe for said first user;

transmitting, by said computing system, said indication data to said cellular telephone belonging to said first user;

generating, by said computing system, a first report indicating results of said first determining and said second determining;

presenting, by said computing system said first report to said first user; and removing said third user profile from said computing system.

The present invention advantageously provides a simple method and associated system capable of preventing individuals from obtaining products that may cause harm.

BRIEF DESCRIPTION OF THE DRAWINGS

FIG. 2 which includes FIGS. 2A and 2B illustrates a flowchart describing an algorithm used by the system of FIG. 1 for preventing users from obtaining products that may cause an allergic reaction, in accordance with embodiments of the present invention.

DETAILED DESCRIPTION OF THE INVENTION

Figure 1:
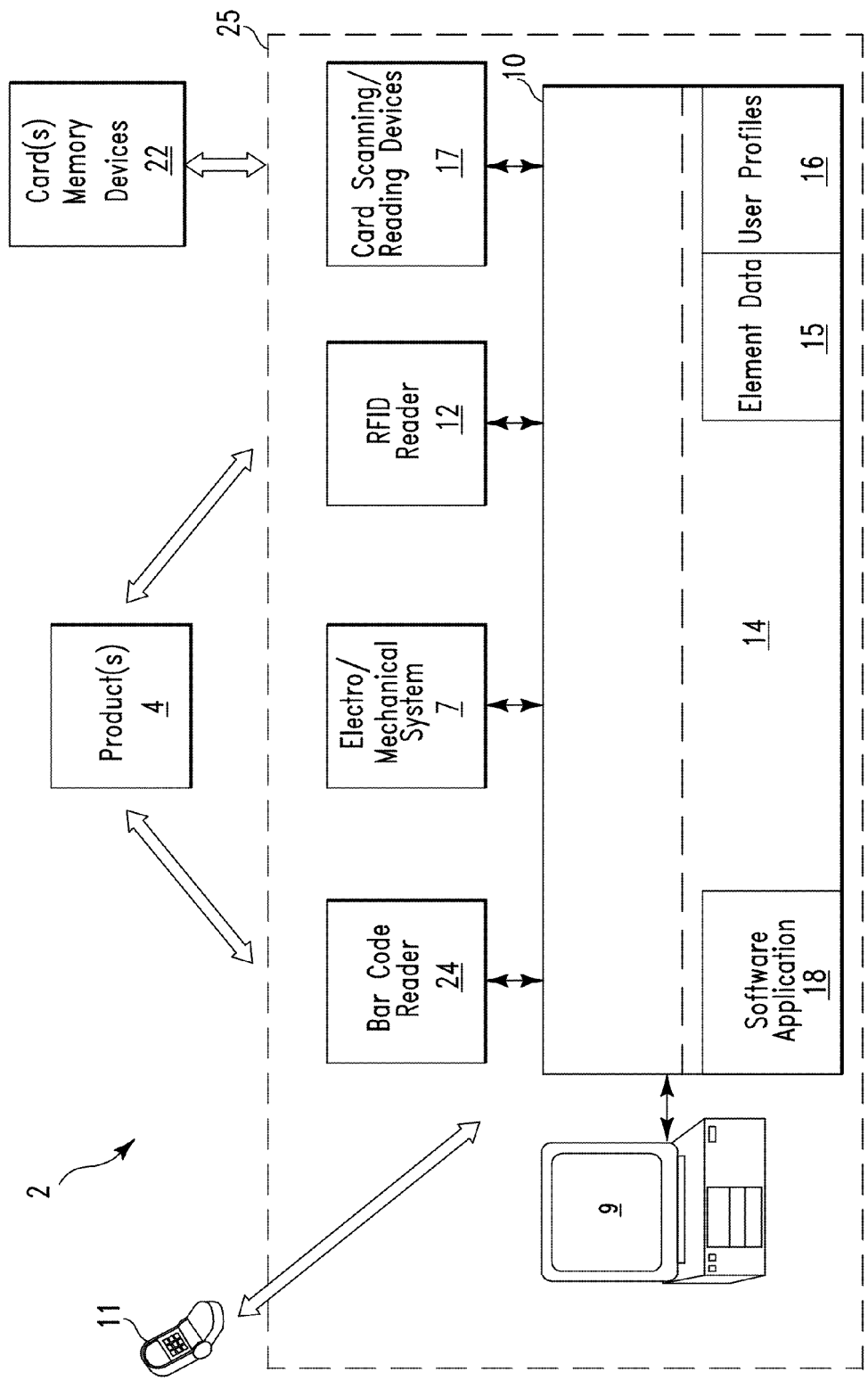
FIG. 1 illustrates a system for preventing users from obtaining products that may cause an allergic reaction, in accordance with embodiments of the present invention.

FIG. 1 illustrates a system 2 for preventing users from obtaining products that may cause an allergic reaction, in accordance with embodiments of the present invention. Individuals that suffer from food allergies must pay attention to allergic-factors associated with products (i.e., compositions/elements of products that may cause allergic reactions) for purchase. Products may include, inter alia, food, medicine, hygiene products (e.g., lotions, shampoo, laundry detergent, etc). Labels for the products may not clearly list all elements/compositions comprised by the products. During a grocery shopping trip, a single user may purchase products for an entire family. Therefore, the user may be required to take into account allergies for all members of the family. System 2 provides a means for preventing an individual from purchasing products that may cause an allergic reaction for the individual and/or his/her family. System 2 is used to match personal (and groups) medical and allergy information of individuals/families with allergic ingredients in products available for purchase.

System 2 of FIG. 1 comprises a computing system 2, a bar code reader 24, electro/mechanical devices 7, an RFID reader 12, card scanning/reading devices 17, an audio/video/computer device 9, a communication device 11, products 4, and cards/memory devices 22. Any combination of computing system 2, bar code reader 24, electro/mechanical devices 7, RFID reader 12, card scanning/reading devices 17, and audio/video/computer device 9 may be located within or attached to a shopping cart 25. Alternatively, any combination of computing system 2, bar code reader 24, electro/mechanical devices 7, RFID reader 12, card scanning/reading devices 17, and audio/video/computer device 9 may be located external to shopping cart 25. Computing system 10 may comprise any type of computing system(s) including, inter alia, a personal computer (PC), a server computer, etc. Computing system 10 comprises a memory system 14. Memory system 14 may comprise a single memory system. Alternatively, memory system 14 may comprise a plurality of memory systems. Memory system 14 comprises a software application 18. Software application 18 enables computing system 10 to retrieve element data 15 associated with products 4 (e.g., food, medicine, hygiene products, etc) via RFID reader 12 and/or bar code reader 24, compare the element data with user profiles 16 (i.e., comprising elements associated with known allergies associated with users) retrieved from cards/memory devices 22 via card scanning/reading devices 17 or communication device 11, and generate warnings in order to warn or prevent the users from purchasing affected products. Additionally, user profile(s) may be transmitted between communication devices. The warning may be presented to the user via audio/video/computer device 9 or communication device 11. Audio/video/computer device 9 may comprise, inter alia, a personal computer, a laptop computer, a video monitor, an audio device, etc. Communication device 11 may comprise any type of communication device including, inter alia, a cellular telephone, a personal digital assistant, a pager, etc. Electro/mechanical system 7 may comprise any type of system that physically prevents a user from placing affected products (i.e., comprising elements associated with known allergies associated with the user) into shopping cart 25. For example, electro/mechanical system 7 may comprise a solenoid (i.e., activated by a control signal supplied by computing system 10) and a door or cover for shopping cart 25. The solenoid is activated when computing system 10 senses a product (of products 4) that comprises elements that that may cause an allergic reaction for a user. The activated solenoid closes the door or cover for shopping cart 25 thereby preventing the user from placing the product into shopping cart 25. Computing system 10 retrieves elements data associated with elements comprised by products 4 via a bar code or a radio frequency identification (RFID) tag located on packaging associated with products 4. A bar code is read by bar code reader 24. An RFID tag is read by RFID tag reader 12. Cards/memory devices 22 may comprise any type of device capable of allowing a user to store user profiles. Cards/memory devices 22 may comprise, inter alia, a fidelity card (a customer rewards card), a SIM card (i.e., a memory card associated with a cellular telephone), a credit card, etc.

The following process steps illustrate a process for preventing users from obtaining products that may cause an allergic reaction performed by system 2:

1. A user enters a profile(s) (i.e., associated with elements associated with known allergies associated with the user and/or individuals associated with the user) within one or more of cards/memory devices 22.
2. The card or memory device is detected by card scanning/reading devices 17 and the profile(s) are loaded into computing system 10.
3. The user moves shopping cart 25 within a specified proximity of a product.
4. A bar code or RFID tag on the packaging for the product is detected via bar code reader 24 or RFID reader 12 and element data associated with the product is retrieved from the bar code or the RFID tag and stored in computing system 10.
5. The element data is compared to the user profile(s) to determine if there is a match.
6. If a match is found, computing system 10 generates a warning for the user. Additionally, computing system 10 may disable the user from purchasing the affected product. Computing system may disable a payment method for purchasing the product or computing system 10 may prevent the affected product from being placed in shopping cart 25 (e.g., using a solenoid and a door on shopping cart 25).
7. If a match is not found, computing system 10 may generate indication data specifying that the product is safe for the user. Additionally, computing system may enable the user to complete a purchase of the product.
8. A report indicating results from steps 6 and 7 may be generated and stored and/or presented to the user (e.g., via audio/video/computer device 9).

Figure 2B:
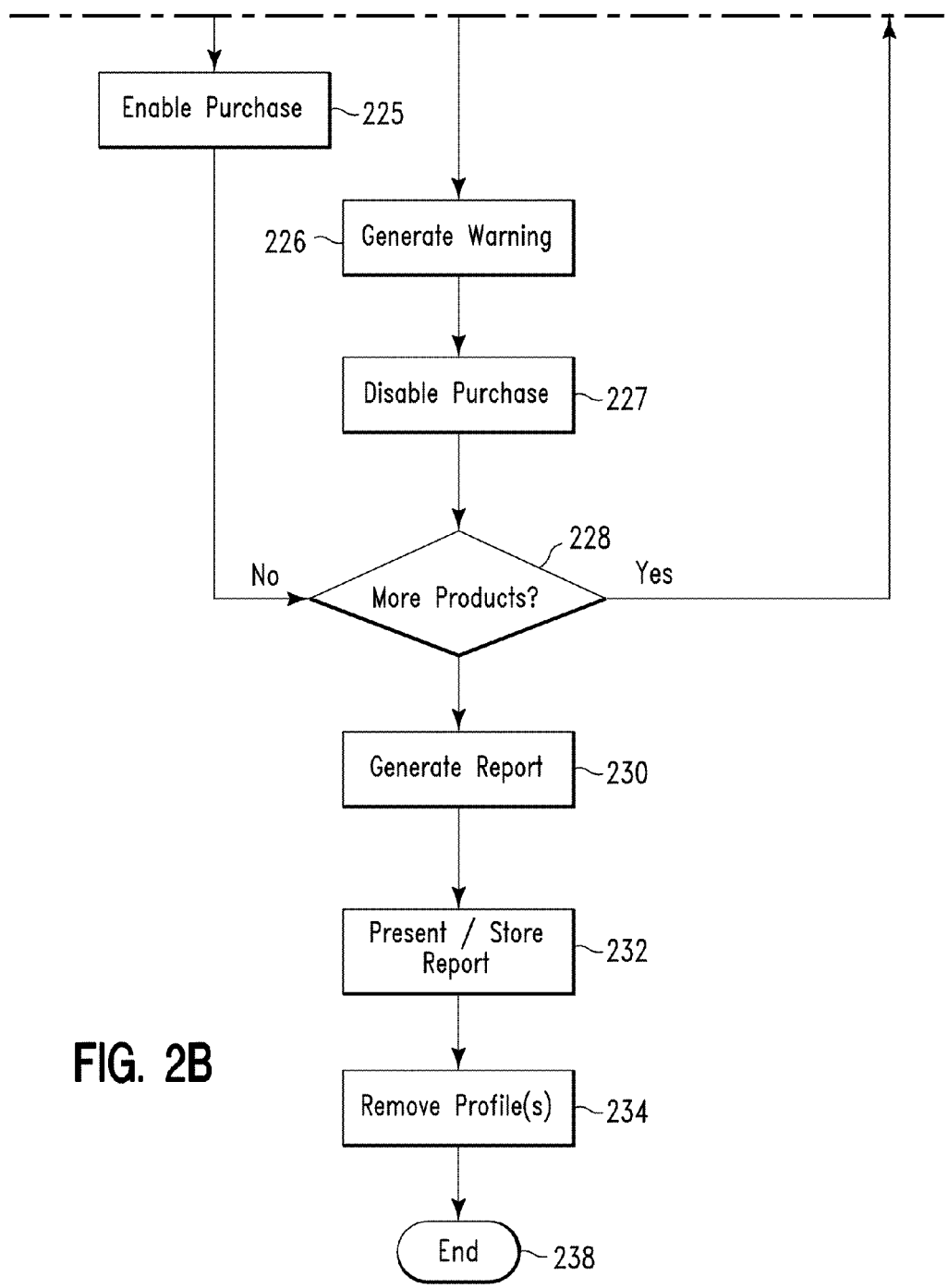

FIG. 2 which includes FIGS. 2A and 2B illustrates a flowchart describing an algorithm used by system 2 of FIG. 1 for preventing users from obtaining products that may cause an allergic reaction, in accordance with embodiments of the present invention. In step 202, a profile(s) (i.e., comprising compositions/elements that may cause allergic reactions for a user and/or a users family or friends) is generated (e.g., by the user, by a doctor, etc). The profile(s) is loaded onto a card (e.g., a fidelity card, a credit card, a debit card, etc) or memory device (e.g., a SIM card, a USB memory device, a flash memory device, etc). The profile(s) may be loaded in using any device including a computer. In step 204, the user enters a retail establishment to purchase products. The user places the card or memory device comprising the profile(s) into a reader (e.g., card scanning/reading devices 17 of FIG. 1). The user enters a command specifying which of the profiles or portions of the profiles should be loaded into the computing system for monitoring. In step 208, a profile, profiles, or portions of profiles are loaded into the computing system. In optional step 210 (i.e., if portions of different profiles are retrieved), the portions of the different profiles are combined into a single profile. In step 214, element data associated with a product is retrieved (i.e., via a bar code or RFID tag). In step 216, the element data from step 214 is compared to the profile(s) from step 208 and/or step 210. In step 220, it is determined if an element (i.e., comprising an allergen) discovered in step 214 matches an element from the profile(s).

If in step 220, it is determined that an element (i.e., comprising an allergen) discovered in step 214 does not match an element from the profile(s) then in step 224 indication data (i.e., indicating a safe product) is generated and presented to the user. In step 225, a purchase for the product is enabled (e.g., a payment method is enabled) and step 228 is executed as described, infra.

If in step 220, it is determined that an element (i.e., comprising an allergen) discovered in step 214 does match an element from the profile(s) then in step 226 a warning (i.e., indicating a dangerous product) is generated and presented to the user. In step 227, a purchase for the product is disabled (e.g., a payment method is disabled) or the computing system may prevent the affected product from being placed in the shopping cart by using a solenoid and a door on shopping cart 25 to block the affected product from being placed in the shopping cart.

In step 228, it is determined if the user will purchase more products. If in step 228, it is determined that the user will purchase more products then step 214 is repeated. If in step 228, it is determined that the user will not purchase more products then in step 230, the computing system generates a report comprising results from the previous steps. In step 232, the report is stored and/or presented to the user. In step 234, the user profile(s) is removed from the computing system and the process terminates in step 238.

Figure 3:
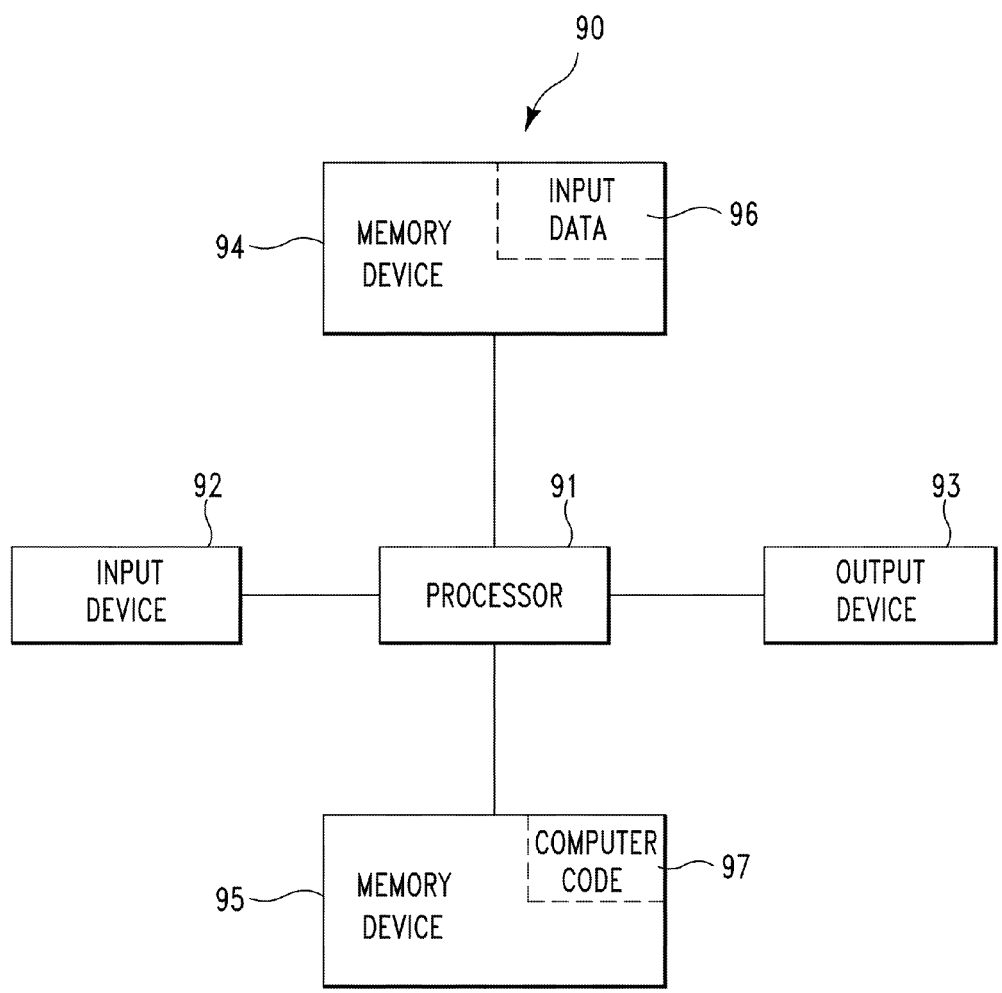
FIG. 3 illustrates a computer apparatus used for preventing users from obtaining products that may cause an allergic reaction, in accordance with embodiments of the present invention.

FIG. 3 illustrates a computer apparatus 90 (e.g., computing system 10 of FIG. 1) used for preventing users from obtaining products that may cause an allergic reaction, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a software application, a mouse, etc. The output device 93 may be, inter alia, a printer, a plotter, a computer screen, a magnetic tape, a removable hard disk, a floppy disk, a software application, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithm of FIG. 2) for preventing users from obtaining products that may cause an allergic reaction. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 3) may comprise the algorithm of FIG. 2 and may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Still yet, any of the components of the present invention could be created, integrated, hosted, maintained, deployed, managed, serviced, etc. by a service provider who offers to prevent users from obtaining products that may cause an allergic reaction. Thus the present invention discloses a process for deploying, creating, integrating, hosting, maintaining, and/or integrating computing infrastructure, comprising integrating computer-readable code into the computer system 90, wherein the code in combination with the computer system 90 is capable of performing a method for preventing users from obtaining products that may cause an allergic reaction. In another embodiment, the invention provides a business method that performs the process steps of the invention on a subscription, advertising, and/or fee basis. That is, a service provider, such as a Solution Integrator, could offer to prevent users from obtaining products that may cause an allergic reaction. In this case, the service provider can create, maintain, support, etc. a computer infrastructure that performs the process steps of the invention for one or more customers. In return, the service provider can receive payment from the customer(s) under a subscription and/or fee agreement and/or the service provider can receive payment from the sale of advertising content to one or more third parties.

While FIG. 3 shows the computer system 90 as a particular configuration of hardware and software, any configuration of hardware and software, as would be known to a person of ordinary skill in the art, may be utilized for the purposes stated supra in conjunction with the particular computer system 90 of FIG. 3. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. An allergy prevention method comprising:

scanning, by a computing system, a fidelity card belonging to a first user;

receiving, by said computing system from said first user, a first command for retrieving a first user profile from said fidelity card, wherein said first user profile comprises information specifying a first plurality of elements known to cause said first user to have an allergic reaction;

retrieving, by said computing system from said fidelity card, said first user profile;

retrieving, by said computing system, first data embedded within a first package associated with a first item for purchase, wherein said first data comprises information specifying a second plurality of elements comprised by said first item;

comparing, by said computing system, said first plurality of elements to said second plurality of elements;

first determining, by said computing system based on said comparing said first plurality of elements to said second plurality of elements, that a first element of said first plurality of elements matches a second element of said second plurality of elements;

generating, by said computing system, a warning indicating to said first user that said first item may cause said first user to have an allergic reaction;

presenting, by said computing system, said warning to said first user;

disabling, by said computing system, said first user from purchasing said first item;

retrieving, by said computing system, second data embedded within a second package associated with a second item for purchase, wherein said second data comprises information specifying a third plurality of elements comprised by said second item;

comparing, by said computing system, said first plurality of elements to said third plurality of elements;

second determining, by said computing system based on said comparing said first plurality of elements to said third plurality of elements, that no elements of said first plurality of elements match any elements of said third plurality of elements;

generating, by said computing system, indication data indicating to said first user that said second item is safe for said first user;

presenting, by said computing system, said indication data to said first user;

enabling, by said computing system, said first user to purchase said second item;

generating, by said computing system, a first report indicating results of said first determining and said second determining;

presenting, by said computing system said first report to said first user; and removing said first user profile from said computing system.

2. The method of claim 1, further comprising:

scanning, by said computing system, said fidelity card belonging to said first user;

receiving, by said computing system from said first user, a second command for retrieving a second user profile from said fidelity card, wherein said second user profile comprises information specifying a fourth plurality of elements known to cause a second user associated with said first user to have an allergic reaction;

retrieving, by said computing system from said fidelity card, said second user profile;
retrieving, by said computing system, third data embedded within a third package associated with a third item for purchase, wherein said third data comprises information specifying a fifth plurality of elements comprised by said third item;
comparing, by said computing system, said fourth plurality of elements to said fifth plurality of elements;
third determining, by said computing system based on said comparing said fourth plurality of elements to said fifth plurality of elements; that a third element of said fourth plurality of elements matches a fourth element of said fifth plurality of elements;
generating, by said computing system, a second warning indicating to said first user that said third item may cause said second user to have an allergic reaction;
presenting, by said computing system, said second warning to said first user;
disabling, by said computing system, said first user from purchasing said third item;
retrieving, by said computing system, fourth data embedded within a fourth package associated with a fourth item for purchase, wherein said fourth data comprises information specifying a sixth plurality of elements comprised by said fourth item;
comparing, by said computing system, said fourth plurality of elements to said sixth plurality of elements;
fourth determining, by said computing system based on said comparing said fourth plurality of elements to said sixth plurality of elements, that no elements of said fourth plurality of elements match any elements of said sixth plurality of elements;
generating, by said computing system, second indication data indicating to said first user that said second item is safe for said second user;
presenting, by said computing system, said second indication data to said first user;
enabling, by said computing system, said first user to purchase said fourth item;
generating, by said computing system, a second report indicating results of said third determining and said fourth determining;
presenting, by said computing system said second report to said first user; and
removing said first user profile from said computing system.

3. The method of claim 1, further comprising:
scanning, by said computing system, a cellular telephone belonging to a second user;
receiving, by said computing system from said second user, a second command for retrieving a second user profile from said cellular telephone, wherein said second user profile comprises information specifying a fourth plurality of elements known to cause said second user to have an allergic reaction;
retrieving, by said computing system from said cellular telephone, said second user profile;
retrieving, by said computing system, third data embedded within a third package associated with a third item for purchase, wherein said third data comprises information specifying a fifth plurality of elements comprised by said third item;
comparing, by said computing system, said fourth plurality of elements to said fifth plurality of elements;
third determining, by said computing system based on said comparing said fourth plurality of elements to said fifth plurality of elements; that a third element of said fourth plurality of elements matches a fourth element of said fifth plurality of elements;
generating, by said computing system, a second warning indicating to said second user that said third item may cause said second user to have an allergic reaction;
presenting, by said computing system, said second warning to said second user;
disabling, by said computing system, said first user from purchasing said third item;
retrieving, by said computing system, fourth data embedded within a fourth package associated with a fourth item for purchase, wherein said fourth data comprises information specifying a sixth plurality of elements comprised by said fourth item;
comparing, by said computing system, said fourth plurality of elements to said sixth plurality of elements;
fourth determining, by said computing system based on said comparing said fourth plurality of elements to said sixth plurality of elements, that no elements of said fourth plurality of elements match any elements of said sixth plurality of elements;
generating, by said computing system, second indication data indicating to said second user that said second item is safe for said second user;
presenting, by said computing system, said second indication data to said second user;
enabling, by said computing system, said second user to purchase said fourth item;
generating, by said computing system, a second report indicating results of said third determining and said fourth determining;
presenting, by said computing system said second report to said second user; and
removing said second user profile from said computing system.

4. The method of claim 1, wherein said presenting said warning to said first user is presented via a video monitor attached to said computing system.

5. The method of claim 1, wherein said presenting said warning to said first user is presented via a cellular telephone belonging to said first user.

6. A computer program product, comprising a computer storage medium comprising a computer readable program code embodied therein, said computer readable program code configured to perform, upon being executed by a processor of said computing system, steps of:
scanning a fidelity card belonging to a first user;
receiving, from said first user, a first command for retrieving a first user profile from said fidelity card, wherein said first user profile comprises information specifying a first plurality of elements known to cause said first user to have an allergic reaction;
retrieving, from said fidelity card, said first user profile;
retrieving first data embedded within a first package associated with a first item for purchase, wherein said first data comprises information specifying a second plurality of elements comprised by said first item;
comparing said first plurality of elements to said second plurality of elements;
first determining, based on said comparing said first plurality of elements to said second plurality of elements, that a first element of said first plurality of elements matches a second element of said second plurality of elements;

generating a warning indicating to said first user that said first item may cause said first user to have an allergic reaction;
presenting said warning to said first user;
disabling said first user from purchasing said first item;
retrieving second data embedded within a second package associated with a second item for purchase, wherein said second data comprises information specifying a third plurality of elements comprised by said second item;
comparing said first plurality of elements to said third plurality of elements;
second determining, based on said comparing said first plurality of elements to said third plurality of elements, that no elements of said first plurality of elements match any elements of said third plurality of elements;
generating indication data indicating to said first user that said second item is safe for said first user;
presenting said indication data to said first user;
enabling said first user to purchase said second item;
generating a first report indicating results of said first determining and said second determining;
presenting said first report to said first user; and
removing said first user profile from said computing system.

7. An allergy prevention method comprising:
scanning, by a computing system in a shopping cart, a SIM card belonging to a first user, wherein said computing system comprises a SIM card reader and an RFID device reader;
receiving, by said computing system from said first user, a first command for retrieving a first user profile from said SIM card, wherein said first user profile comprises information specifying a first plurality of elements known to cause said first user to have an allergic reaction;
retrieving, by said computing system from said SIM card, said first user profile;
retrieving, by said computing system, first data embedded within a first RFID tag attached to a first package associated with a first item for purchase, wherein said first data comprises information specifying a second plurality of elements comprised by said first item;
comparing, by said computing system, said first plurality of elements to said second plurality of elements;
first determining, by said computing system based on said comparing said first plurality of elements to said second plurality of elements; that a first element of said first plurality of elements matches a second element of said second plurality of elements;
generating, by said computing system, a warning indicating to said first user that said first item may cause said first user to have an allergic reaction;
presenting, by said computing system, said warning to said first user;
disabling, by said computing system, said first user from placing said first item in said shopping cart;
retrieving, by said computing system, second data embedded within a second RFID tag attached to a second package associated with a second item for purchase, wherein said second data comprises information specifying a third plurality of elements comprised by said second item;
comparing, by said computing system, said first plurality of elements to said third plurality of elements;
second determining, by said computing system based on said comparing said first plurality of elements to said third plurality of elements, that no elements of said first plurality of elements match any elements of said third plurality of elements;
generating, by said computing system, indication data indicating to said first user that said second item is safe for said first user;
presenting, by said computing system, said indication data to said first user;
enabling, by said computing system, said first user to place said second item into said shopping cart;
generating, by said computing system, a first report indicating results of said first determining and said second determining;
presenting, by said computing system said first report to said first user; and
removing said first user profile from said computing system.

8. The method of claim 7, further comprising:
scanning, by said computing system, said SIM card belonging to said first user;
receiving, by said computing system from said first user, a second command for retrieving a second user profile from said SIM card, wherein said second user profile comprises information specifying a fourth plurality of elements known to cause a second user associated with said first user to have an allergic reaction;
retrieving, by said computing system from said SIM card, said second user profile;
retrieving, by said computing system, third data embedded within a third RFID tag attached to a third package associated with a third item for purchase, wherein said third data comprises information specifying a fifth plurality of elements comprised by said third item;
comparing, by said computing system, said fourth plurality of elements to said fifth plurality of elements;
third determining, by said computing system based on said comparing said fourth plurality of elements to said fifth plurality of elements; that a third element of said fourth plurality of elements matches a fourth element of said fifth plurality of elements;
generating, by said computing system, a second warning indicating to said first user that said third item may cause said second user to have an allergic reaction;
presenting, by said computing system, said second warning to said first user;
disabling, by said computing system, said first user from placing said first item in said shopping cart;
retrieving, by said computing system, fourth data embedded within a fourth RFID tag attached to a fourth package associated with a fourth item for purchase, wherein said fourth data comprises information specifying a sixth plurality of elements comprised by said fourth item;
comparing, by said computing system, said fourth plurality of elements to said sixth plurality of elements;
fourth determining, by said computing system based on said comparing said fourth plurality of elements to said sixth plurality of elements, that no elements of said fourth plurality of elements match any elements of said sixth plurality of elements;
generating, by said computing system, second indication data indicating to said first user that said fourth item is safe for said second user;
presenting, by said computing system, said second indication data to said first user;
enabling, by said computing system, said first user to place said fourth item into said shopping cart;

generating, by said computing system, a second report indicating results of said third determining and said fourth determining;
presenting, by said computing system said second report to said first user; and
removing said first user profile from said computing system.

9. The method of claim 7, further comprising:
scanning, by said computing system, a cellular telephone belonging to a second user;
receiving, by said computing system from said second user, a second command for retrieving a second user profile from said cellular telephone, wherein said second user profile comprises information specifying a fourth plurality of elements known to cause said second user to have an allergic reaction;
retrieving, by said computing system from said cellular telephone, said second user profile;
retrieving, by said computing system, third data embedded within a third package associated with a third item for purchase, wherein said third data comprises information specifying a fifth plurality of elements comprised by said third item;
comparing, by said computing system, said fourth plurality of elements to said fifth plurality of elements;
third determining, by said computing system based on said comparing said fourth plurality of elements to said fifth plurality of elements; that a third element of said fourth plurality of elements matches a fourth element of said fifth plurality of elements;
generating, by said computing system, a second warning indicating to said second user that said third item may cause said second user to have an allergic reaction;
presenting, by said computing system, said second warning to said second user;
disabling, by said computing system, said first user from purchasing said third item;
retrieving, by said computing system, fourth data embedded within a fourth package associated with a fourth item for purchase, wherein said fourth data comprises information specifying a sixth plurality of elements comprised by said fourth item;
comparing, by said computing system, said fourth plurality of elements to said sixth plurality of elements;
fourth determining, by said computing system based on said comparing said fourth plurality of elements to said sixth plurality of elements, that no elements of said fourth plurality of elements match any elements of said sixth plurality of elements;
generating, by said computing system, second indication data indicating to said second user that said second item is safe for said second user;
presenting, by said computing system, said second indication data to said second user;
enabling, by said computing system, said second user to purchase said fourth item;
generating, by said computing system, a second report indicating results of said third determining and said fourth determining;
presenting, by said computing system said second report to said second user; and
removing said second user profile from said computing system.

10. The method of claim 7, wherein said presenting said warning to said first user is presented via a video monitor attached to said computing system.

11. The method of claim 7, wherein said presenting said warning to said first user is presented via a cellular telephone belonging to said first user.

12. An allergy prevention method comprising:
scanning, by a computing system in a shopping cart, a SIM card belonging to a first user, wherein said computing system comprises a SIM card reader, a fidelity card/credit card reader, and an RFID device reader;
receiving, by said computing system from said first user, a first command for retrieving a first user profile from said SIM card, wherein first user profile comprises first information specifying a first plurality of elements known to cause said first user to have an allergic reaction;
retrieving, by said computing system from said SIM card, said first user profile;
scanning, by said computing system, a fidelity card/credit card belonging to said first user;
receiving, by said computing system from said first user, a second command for retrieving a second user profile from said fidelity card/credit card, wherein said second user profile comprises second information specifying a second plurality of elements known to cause said first user to have an allergic reaction;
retrieving, by said computing system from said fidelity card/credit card, said second user profile;
generating, by said computing system, a third user profile from said first user profile and said second user profile;
retrieving, by said computing system, first data embedded within a first RFID tag attached to a first package associated with a first item for purchase, wherein said first data comprises information specifying a third plurality of elements comprised by said first item;
comparing, by said computing system, said first plurality of elements and second plurality of elements to said third plurality of elements;
first determining, by said computing system based on said comparing said first plurality of elements and second plurality of elements to said third plurality of elements; that a first element of said first plurality of elements matches a second element of said third plurality of elements;
generating, by said computing system, an audible warning indicating to said first user that said first item may cause said first user to have an allergic reaction;
transmitting, by said computing system, said audible warning to a cellular telephone belonging to said first user;
enabling, by said computing system, a first solenoid attached to a door on said shopping cart resulting in shutting said door and preventing said user from placing said first item in said shopping cart;
sensing, by said computing system, that said first item in not within a specified proximity said shopping cart;
disabling, by said computing system, said first solenoid resulting in opening said door and allowing said user to place items in said shopping cart;
retrieving, by said computing system, second data embedded within a second RFID tag attached to a second package associated with a second item for purchase, wherein said second data comprises information specifying a fourth plurality of elements comprised by said second item;
comparing, by said computing system, said first plurality of elements and second plurality of elements to said fourth plurality of elements;
second determining, by said computing system based on said comparing said first plurality of elements and second plurality of elements to said fourth plurality of elements, that no elements of said first plurality of elements and second plurality of elements match any elements of said fourth plurality of elements;

generating, by said computing system, indication data indicating to said first user that said second item is safe for said first user;

transmitting, by said computing system, said indication data to said cellular telephone belonging to said first user;

generating, by said computing system, a first report indicating results of said first determining and said second determining;

presenting, by said computing system said first report to said first user; and removing said third user profile from said computing system.

13. The method of claim 12, further comprising:

generating, by said computing system, a video warning indicating to said first user that said first item may cause said first user to have an allergic reaction; and presenting, by said computing system, said video warning to said first user via a video monitor comprised by said computing system.

* * * * *